(12) United States Patent
Hartfeldt

(10) Patent No.: US 7,141,605 B2
(45) Date of Patent: Nov. 28, 2006

(54) METHOD OF CONTROLLING ANIMAL PESTS AND DISINFECTING INANIMATE SURFACES

(75) Inventor: Will H. Hartfeldt, Edina, MN (US)

(73) Assignee: Phyton Corporation, Edina, MN (US)

( * ) Notice: Subject to any disclaimer, the term of this patent is extended or adjusted under 35 U.S.C. 154(b) by 166 days.

(21) Appl. No.: 10/705,688

(22) Filed: Nov. 10, 2003

(65) Prior Publication Data

US 2004/0138144 A1    Jul. 15, 2004

Related U.S. Application Data

(62) Division of application No. 09/610,920, filed on Jul. 6, 2000, now Pat. No. 6,646,000.

(60) Provisional application No. 60/142,506, filed on Jul. 6, 1999.

(51) Int. Cl.
*A01N 55/02*     (2006.01)
*A01N 25/22*     (2006.01)
*A01N 33/22*     (2006.01)
*A01N 37/02*     (2006.01)
*A01N 43/02*     (2006.01)
*A01N 43/04*     (2006.01)

(52) U.S. Cl. .......................... 514/500; 514/23; 514/25; 514/27; 514/450; 514/451; 514/453; 514/456; 514/460; 514/499; 514/533; 514/557; 514/728; 514/970; 514/973; 424/630; 424/638; 424/714; 422/28

(58) Field of Classification Search .................. 422/28; 514/25, 27, 450, 451, 453, 456, 460, 499, 514/500, 533, 557, 728, 23, 970, 973; 424/630, 424/638, 714
See application file for complete search history.

(56) References Cited

U.S. PATENT DOCUMENTS 4,544,666 A * 10/1985 Thirumalachar et al. .... 514/460

\* cited by examiner

*Primary Examiner*—John Pak
(74) *Attorney, Agent, or Firm*—Craig Gregersen

(57) ABSTRACT

A method of treating plant and animal systems and inanimate surfaces for the purposes of controlling plant pests, introducing pesticides and nutrients into plants, mitigating frost damage to plants, increasing crop yields, controlling certain plant diseases, controlling arthropod, bacterial, fungal, mycoplasma, rickettsia, and viral pests of animals and humans, and disinfecting inanimate surfaces. The method utilizes the unique multi-directional dispersion property of the tannate complex of picro ammonium formate and the tannate complex of picro cupric ammonium formate, in aqueous solution, combined with a minor amount of a surfactant sufficient to prevent formation of ammonium picrate, to penetrate plant and animal systems and inanimate surfaces and travelling multidirectionally therein. The method is carried out by introducing a small but effective amount of the tannate complex to the plant or animal system or inanimate surface.

5 Claims, No Drawings

METHOD OF CONTROLLING ANIMAL PESTS AND DISINFECTING INANIMATE SURFACES

CROSS REFERENCE TO RELATED APPLICATIONS

This application is a division of U.S. application Ser. No. 09/610,920 filed Jul. 6, 2000, now U.S. Pat. No. 6,646,000. Application Ser. No. 09/610,920 claims the benefit of U.S. Provisional Application Ser. No. 60/142,506 filed Jul. 6, 1999.

FIELD OF THE INVENTION

This invention is directed to the utilization of heretofore undiscovered unique properties of two known anti-microbial agents used on plants: (A) a fungicide and bactericide for the control of additional pests and maladies, and for other benefits to the host, such as (1) control of insects and other pests of plants, (2) transport multi-directionally within plants while carrying nutrients and other materials there, while functioning as a source of plant nutrition, in addition to being pesticidal, (3) inducement of improved plant health by stimulating the plant's own health system, a process sometimes called "systemic activated resistance" (SAR), (4) synergistic effect when combined with certain other pesticides (5) disinfection of inanimate surfaces proximate to plants or humans or animals, (6) control of certain pests and diseases by topical application where the hosts are animals and humans, and (B) another anti-microbial agent with a similar range of undiscovered properties.

BACKGROUND OF THE INVENTION

U.S. Pat. No. 4,673,687 discloses a chemotherapeutic agent composed essentially of the tannate complex of picro cupric ammonium formate in aqueous solution combined with a minor amount of a surfactant sufficient to prevent formation of ammonium picrate. The therapeutic agent, identified as KT-19827 (and sold under the registered trademark PHYTON-27), is disclosed as useful in the control of plant diseases caused by pathogenic fungi and bacteria.

That patent, which is a division of the application which issued as U.S. Pat. No. 4,544,666, also discloses another chemotherapeutic agent, identified as KT-198, which is composed essentially of a tannate complex of picro ammonium formate and surfactant in a minor amount, which is disclosed as useful in control of plant diseases caused by pathogenic rickettsia-like organisms (RLO's), mycoplasma-like organisms (MLO's), and plant viruses.

It has been discovered that KT-19827 and KT-198 have the unexpected ability to pass through cell walls and kill certain arthropods; arachnids, such as mites; insects, such as aphids and whiteflies; certain mollusks, such as slugs; and certain other animals such as nematodes and similar pests which afflict the foliage, stems, roots, blossoms and seeds of plants. This property enables KT-19827 and KT-198 to be used by application to plants or to the soil around plants to control the numbers of these plant pests. It has also been discovered that KT-19827 and KT-198 can be of significant nutritive value to the plants treated.

U.S. Pat. No. 4,678,687 discloses the ability of KT-19827 and KT-198 to quickly translocate from the injection site in a tree through the entire tree from the roots to the crown leaves. It has now been discovered that unexpectedly this property is broader and includes dispersal in all directions not limited to elongated translocational cells composing the vascular system. It may be utilized to carry other substances, such as nutrients, admixed with KT-19827 or KT-198 to distribute the added substance from the application site throughout a treated plant, shrub or tree, for delivery to the points of use via the plant's own internal transport system. The ability of KT-19827 and KT-198 to penetrate plant cell walls and move among cells in multiple directions may be utilized to introduce substances such as nutrients to the plant, as by spraying or dipping, at standard rates and intervals prescribed by the US EPA label for pesticidal efficiency without doing plant damage.

Disinfection of inanimate surfaces proximate to plants or humans or animals is an unexpected use, which derives from the discovered high level of free copper ions, $Cu++$. High ionic copper levels equate to greater efficacy against bacterial and other pathogens. The low total copper as metallic needed for efficacy against bacterial and other pathogens assures that it can be obtained without copper damage to plants proximate to the disinfected site.

The ability of KT-19827 and KT-198 to pass through cell walls and kill certain pests enumerated above also enables KT-19827 and KT-198 to be used to control other pests found in and around structures for habitation by humans and animals; control of animal pests such as bird lice, and control of human pests such as mites and head lice, fungal infections of the feet, microbial infections of cartilage and other sternum locales exposed to hospital infections during surgery which do not respond, due to low or no blood-circulation, to standard antibiotics ingested or given intravenously.

THE PRIOR ART

U.S. Pat. No. 4,673,6817 issued Jun. 16, 1987.
U.S. Pat. No. 4,544,666 issued Oct. 1, 1985.
Hammer, P. E., 1988, Post-harvest control of *Botrytis cineria* on cut roses with picro-cupric-ammonium formate. Plant Dis., 72: 347–350.

SUMMARY OF THE INVENTION

Broadly stated this invention is directed to the method of controlling plant pests which comprises applying to the plant afflicted with the pests, or to the unwanted primitive plants, a dilute aqueous solution of the tannate complex of picro cupric ammonium formate combined with a minor amount of a surfactant sufficient to prevent formation of ammonium picrate, identified as KT-19827 or by treatment with a dilute aqueous solution of the tannate complex of picro ammonium formate combined with a minor amount of a surfactant sufficient to prevent the formation of ammonium picrate, identified as. KT-198.

The invention is directed as well to the method of increasing plant crop yield by nourishing a plant by introducing to the plant a dilute aqueous solution of KT-19827 or KT-198 alone or supplemented with dissolved plant nutrients applied as foliar sprays, soil drench or vascular injection.

The invention is also directed to the method of improving plant health by applying KT-19827 or KT-198 to prevent frost damage, to induce dessication of partially frost damaged tissue, and to stimulate adjoining viable tissue.

Additionally, the invention is also directed to the method of improving plant health by stimulating the plant's own health system, benefits sometimes called systemic activated resistance, (SAR) to disease, achieved by treatment of plants with a dilute aqueous solution of KT-19827 or KT-198.

The invention is also directed to the method of improving control of plant diseases and pests through synergistic improvements achieved by combining KT-19827 or KT-198 with other commercially available pesticidal products.

Also the invention is directed to the method of disinfection of inanimate surfaces proximate to plants by treatment with unexpectedly dilute aqueous solutions of KT-19827 or KT-198.

The invention is directed to the method of controlling arachnids, insects, bacterial, fungal, slugs, nematodes, mycoplasma (including spiroplasma), rickettsia, and viral pests of animals and humans. These benefits are achieved by topical treatment of exposed surfaces with KT-19827 or KT-198.

DETAILED DESCRIPTION OF THE PREFERRED EMBODIMENTS

The properties and method of production of KT-19827 are described in detail in U.S. Pat. No. 4,670,687 and No. 4,544,666. These descriptions are incorporated herein by reference.

The invention is described in detail with particular reference to the control of plant pests, including but not limited to flies, mites, beetles, ants, nematodes, aphids, mealy bugs, thrips, slugs, and the like which afflict food and ornamental plants (both field grown and grown in greenhouses) including but not limited to food plants such as tomatoes, strawberries, pears, grapes, apples and other rosaseae, peppers, eggplants, potatoes, squash, rutabagas, bananas, pineapples, rice, beets, cucumbers, and the like, flowers such as roses, marigolds, poinsettias, geraniums, impatiens, pansies, orchids, violets, azaleas, lilies, peonies, cyclamen, iris, chrysanthemums, carnations, hibiscus, ferns, tropical foliage, and the like, trees such as oaks, maples, sycamores, willows, aspens, lindens, locusts, conifers, and the like, and shrubs and vines such as lilacs, forsythia, spirea, barberry, bougainvillea, Indian hawthorne, dogwood, cherry, laurel, hydrangea, and the like.

KT-19827 and KT-198 are applied in aqueous solution, most generally by spraying, or dipping or soil drenching when appropriate. Application rates and repetition of application depend upon the particular pest being controlled, pest pressure, host plant conditions, host plant safety parameters, and the like. Most generally the control agent is applied to plants at a rate of about 12 to 55 ounces per 100 gallons of water, but preferably between about 15 and 30 ounces per 100 gallons. While limited control may be achieved at lower rates of application, most effective control results from application at middle rates within the preferred range. The aqueous solution preferably has a pH between about 7.0 and 5.8, which results from the addition of KT-19827 and KT-198 which have a pH of 4.7, to water within the prescribed ranges. The material is preferably applied in an amount sufficient to completely wet the affected plant surfaces to the point of run-off for maximum effectiveness. For disinfecting inanimate surfaces the material is applied at a lower rate between about 4 to 15 ounces per 100 gallons of water and preferably between about 4 to 8 ounces per 100 gallons of water.

Standard commercial hydraulic spray equipment (such as Dramm) or chemigation equipment may be used. Such equipment is usually pressurized by compressed air or carbon dioxide. The foliage should be fluffed by the force of the spray to optimize cover of underleaves. The use of ESS (electrostatic) fine particle sprayers and other foggers is less preferred. Although these methods assure total coverage, the quantity of KT-19827 deposited may be inadequate in some circumstances, such as where infection is well underway and therapeutic treatment is required. Aerial applications may be made to field and forest settings.

In the event of an entrenched infestation involving several life stages of the pest, more than one application may be needed. The preferred interval between applications is 10 days. Good plant safety permits intervals as short as 3 to 5 days. A mild infestation may require retreatment in 21 days or monthly as long as conditions are conducive to continuing pest pressure.

Spray pressure pounds per square inch (psi) is preferred at about 250 but can be used by experienced operators at 350 psi or more. There is no minimum requirement for spray pressure. Backpack and hand sprayers, which are aimed directly at the host plant rather than lofted over them, can be used. Because there is a risk of chemical decomposition if the spray solution is not used within 48 hours, only as much as is needed should be diluted for use. Galvanized metal and aluminum exposure via spray containers or pipes may alter the spray and present a risk to plant safety.

The preferred rate of KT-19827 and KT-198 on all insects infesting all crops is 20 fluid ounces of the liquid concentrate per 100 U.S. gallons potable water. Plant safety is the primary consideration. This rate is generally efficacious and safe to plants, except open blooms for which the limit is 15 fluid ounces to 100 gallons. Because senescing blooms are damaged first and buds are unaffected by high doses, in the event of a substantial infestation the applicatior may choose to sacrifice aging blooms or use two applications at the lower rate 2 or 3 days in succession as the way to deliver a lethal dose without damage. Higher rates may be needed in some circumstances. However, care should be taken at rates about 35 fl oz per 100 gallons by trying a small amount of the host plant to check for plant safety.

Plant sites where the invention can be used are very broad because plant safety of KT19827 has been previously established on greenhouse crops such as but not limited to pot crops, bedding plants, foliage, bulbs and cut flowers. Examples of each are poinsettia, geraniums, spathyphyllum, tulips and cut roses, respectively. Safety has also been established previously on plants located in interiorscapes and woody ornamentals such as but not limited to azaleas, lilac, entomosporium and rosasceae. Also safe are a wide range of deciduous and coniferous trees, which may be treated in the landscape, the forest and the nursery. Examples are Japanese Maples and Austrian Pines, respectively. It is also known that KT-19827 can be applied to food crops such as fruit trees and vines, tropical fruit crops, specialty row crops and field crops. Examples are pear trees, grapevines, mangos, tomatoes and potatoes, respectively.

Applications should follow good practice. For example, sprays in the heat of the day or when plants will remain wet overnight are inadvisable. Because KT-19827 is systemic, rain, spray irrigation and misting do not wash it off once dry. Sprays applied with standard commercial greenhouse equipment can also be used for controlling spider mites, other insects and also against nematodes, which are commonly shielded and embedded with the tissue of their host and difficult to control at dosages low enough to avoid phytotoxicity. KT-19827 can enter plant tissue where nematodes are embedded. For foliar nematodes, a foliar spray is applied at the rate of 32 fluid ounces per 100 U.S. gallons water and for spider mites, KT-19827 is applied at a rate of 26 fluid ounces per 100 U.S. gallons water. Nematodes located within the root structure and soil-borne but feeding on the plant's root structure may also be treated but with a soil drench at the higher rate of 35 fluid ounces per 100 gallons water. The volume of solution applied should equal the amount of water needed for a thorough watering. The whole rooted area should be drenched, with special attention to the area immediately surrounding the main stem(s).

White flies and spider mites are serious and sometimes uncontrollable pests of food and ornamental crops (both field grown and grown in greenhouses) throughout the world. They are a persistent problem and develop resistance to insecticides and miticides which can be mitigated by (a) the introduction of different cidal materials, (b) by timely applications made preventively before populations get out of hand just prior to harvesting crops and shipping flower crops to avoid transport to new venues and product quality degradation.

The discovery that KT-19827 and KT-198 are unexpectedly effective against these pests and others, as well as against microbes as previously disclosed, provides a method of dual control to the grower. This reduces labor and the amount of chemicals applied to the crop. It makes possible a preventive application concurrently and in the course of applications for microbial disease control. In the case of flower crops, such as poinsettia, this concurrent treatment is particularly valuable because the maladies can and do strike in the final days of the crop when it is in full bloom and easily damaged by chemicals or marred by visible residue.

The ability of KT-19827 or KT-198 to carry other substances while being dispersed in many directions within the plant is unexpected. Tests have shown significant movement laterally, downward, and upward when plant parts not treated with a foliar spray or soil drenched are analyzed for copper levels. The extent of this movement varies among plant species. This movement makes possible the internal dispersal of pesticides and micronutrients which are not phytotoxic and which were previously limited to topical applications or limited to dispersal via the plant's vascular system. This distribution can result in economical, lower dosages of such products. Examples of pesticides which may be transported include Avermectin miticide, pyrethrin insecticides, neem oil-based insecticides. Exemplary micronutrients include iron, manganese, zinc and boron in amounts calculated to not exceed recommended limits in the target plant biomass when added to existing levels.

KT-19827 and KT-198 themselves enhance the plant's productivity while providing pesticidal benefit. For example, production of tomatoes, pears, grapes and other fruits and vegetables can be increased by 20–30% with several foliar spray application of KT-19827. In another illustration, when KT-19827 is sprayed onto frost damaged areas, it helps the plant recover as it delivers nutrients to the viable tissue abutting the damage. It also mitigates post-frost damage by killing opportunistic bacteria and fungi, and desiccated disease damaged tissue to eliminate further pathogen foodstuff.

Another related benefit to crop productivity leads to a longer period free of recurring disease due to the ability of KT-19827 to activate systemic resistance by the treated plant. This has been unexpectedly observed in geraniums, which resist the reappearance of *Xanthomonas* disease symptoms and pear trees, where the phenomenon is in the context of *Erwinia*, both of which examples are set forth below.

KT-19827 can be used to obtain increased crop yield and disease control without damage to tender tissue. This was demonstrated on pear trees plagued with *Erwinia* (Fireblight). A series of foliar sprays was applied before, during and after bloom and later in the season as needed. *Erwinia* was controlled without damage to tender blooms, and the pear crop was significantly larger and unblemished. This unexpected, unusual multiple benefit indicates a phytotherapeutic defense wherein the copper molecule, it is believed, is rendered metabolizable by the plant, thereby enhancing its own defense characteristics. The molecule of copper is rendered systemic so that its action is accomplished, most importantly, inside the treated plants. Thus a continuity of protection and a reinvigorating effect on the plant are assured, which is evidenced by the quantity and unblemished quality of the fruit.

KT-19827 can be used to disinfect inanimate surfaces such as ebb and flow benches in a greenhouse because the low dosage of 4 ounces per 100 gallons of water makes it safe for plants, such as potted calla lilies growing on *Erwinia*-infected benches, despite the continuing exposure to the recycling fertigation fluid. This characteristic of KT-19827 is unexpected compared to currently available copper bactericides, which are effective as surface and water disinfectants but only at rates phytotoxic to plants. The unique characteristic also makes possible control of algae in or on the growing media of plants without causing plant injury. This same parameter makes possible the control of algae and, mosses growing in and around plants, such as turf. It has been discovered that effectiveness at such low rates correlates with an unexpectedly high rate of free copper ions in KT-19827 per unit of copper compared to other copper disinfectants.

The invention is also directed to the method of controlling arthropod, bacterial, fungal (including yeasts such as *Cryptcoccus neoformans*), mycoplasma (including spiroplasma and *Histoplasma*), rickettsia, and viral pests of animals and humans. These benefits are achieved by topical treatment of exposed surfaces or areas contaminated by yeasts such as *Cryptococcus neoformans* or *Histoplasma* in bird droppings, application to the human or animal epidermis for control of lice or to surgically exposed surfaces with KT-19827 or KT-198 for control of microbes such as *Staphylococcus, Enterococci*, "traditional gram negatives" including *Pseudomonas, aeruginosa, Enterobacter species*, and *Candida* species.

The invention is further illustrated by the following examples:

EXAMPLE A-1

Spider Mite Control on Potted Roses and Marigolds

Mites are a serious pest of plants grown throughout the world. An experiment determined the effectiveness of KT-19827 in controlling the two spotted spider mite, *Tetranychus urticae* on greenhouse-grown miniature roses of the variety "Golden Sunblaze" in 6 inch pots. KT-19827 was applied once, at either 1.3 fluid ounces., or 2.6 fluid ounces per 10 gallons of finished spray using a carbon dioxide compressed gas sprayer at 40 psi. It was compared to untreated control plants or plants treated with the commercial miticide, Avermectin, (Avid) at 0.4 oz. Per 10 gallons. There were six replicate plants per treatment. Adult and nymph spider mites were counted on three areas of each plant (upper, middle, lower). The sum of these three measurements is presented. Results show that KT-19827 at the 2.6 ounce rate provided a level of spider mite control comparable to the commercial standard.

Mean Number of Adult and Nymph Mites*

| Treatment | Rate | 6 Days After Treatment | 10 Days After Treatment | 16 Days After Treatment |
|---|---|---|---|---|
| Untreated | — | 29.9a | 27.4a | 108.3a |
| Avermectin | 0.4 oz. | 0b | 0.2b | 0.7b |
| KT-19827 | 1.3 oz. | 4.0b | 11.0b | 33.8b |
| KT-19827 | 2.6 oz. | 0.3b | 0b | 0b |

*Means in a column with letter in common are not significantly different.

Another experiment was conducted on Marigolds in 6-inch pots. KT-19827 was applied at 2.5 or 1.24 fluid ounces per 10 gallons of finished spray using a hand-held compressed air sprayer at 35 psi. It was compared to untreated controls, the commercial miticide Avermectin (Avid, Merck) at 0.4 ounces per 10 gallons, and the commercial Neem-based insecticide Triact 90 at 10.0 mL per liter. There were 6 replications. Plant samples of 5 leaves were taken randomly from upper to lower plant areas. The experiment showed results comparable to the commercial products.

Table of Results on Marigolds

| Treatment | Precount | Week 1 | Week 2 | Week 3 |
|---|---|---|---|---|
| Check | 35.0b | 11.6ab | 96.4ab | 171.4a |
| Avermectin | 14.6b | 0.0b | 6.2c | 23.8c |
| Phyton-27 2.0 ml | 17.8b | 0.6b | 34.8bc | 76.4bc |
| Phyton-27 1.0 ml | 23.8b | 2.8b | 42.0abc | 112.6ab |
| Neem Oil 10.0 ml | 18.8b | 2.6b | 6.4c | 33.6c |

The researcher stated the following conclusions:

The Phyton-27 treatments had quick knockdown impact on the mite population. In the first week there was an excellent reduction in mite populations. There were mites in the area, which led to re-infestation of the test plot in the second and third weeks. If this was not present, the population would not have rebounded and there would have been good control. It appears that two applications a week or two apart should definitely give excellent control.

EXAMPLE A-2

Control of White Flies on Poinsettia

An experiment was conducted to determine the effectiveness of KT-19827 in controlling white flies on poinsettia. KT-19827 was applied at 2.6 oz. per 10 gallons. It was compared to untreated plants or plants treated with the commercial insecticides Bifenthrin, Neem Oil or Acephate. KT-19827 at the 2.6 oz. rate provided a level of whitefly control comparable to the commercial standards:

Mean Number of White Flies*

| Treatment | Rate | 6 Days After Treatment | 10 Days After Treatment |
|---|---|---|---|
| Untreated | — | 100.3 | 42.3 |
| Acephate | 0.5 | 26.8 | 44.5 |
| Bifenthrin | 0.1 | 27.7 | 8.7 |
| Neem Oil | 0.033 | 29.5 | 29.3 |
| KT-19827 | 2.6 | 34.0 | 34.8 |

*Means represent the number of living whitefly immatures per leaf.

In another study, twenty poinsettia plants were planted into 6.0 inch containers and were grown in a greenhouse and arranged in a completely randomized design (CRD). Treatments were KT-19827 at 2.5 fluid ounces per 10 gallons water, chlorpyrifos (Duraguard) at 25.0 fluid ounces per 100 gallons water as a treated check, and an untreated check. Plants were sprayed to run-off with the appropriate treatments when they had a moderate to heavy infestation of silverleaf whitefly, *Bemista argentifolii*. Plants were sampled before (precount) and 3 days after treatment (DAT) by randomly harvesting 10 leaves from each plant and then counting the number of live and dead whitefly nymphs.

All data were analyzed in a completely randomized design using a two-way analysis of variance (ANOVA) for the number of live whitefly nymphs and percent mortality 3 days after treatment. Percent mortality was determined by dividing the number of dead whiteflies by the total number of whiteflies (alive and dead).

| Treatments | Rate (oz/10 gal. of water) | Precount (live whitefly nymphs | Live Whitefly nymphs (3 DAT) | % Mortality (3DAT) |
|---|---|---|---|---|
| KT-19827 | 2.5 | 426.0 | 138.5bc | 35.1ab |
| Chlorpyrifos | 2.5 | 342.5 | 143.0bc | 34.0ab |
| Untreated | — | 307.0 | 321.8ab | 7.0b |

The KT-19827 treatment was significant as a knockdown of live whitefly nymphs 3 days after treatment (DAT), and was comparable to a standard insecticide treatment, chlorpyrifos.

EXAMPLE A-3

Control of Nematodes

The plant damage from nematodes is difficult to control. Nematodes are commonly shielded and embedded within the tissue of their host. They also tend to be resistant to pesticides at dosages low enough to avoid phytotoxicity. KT-19827 (Phyton-27) can be effective because of its ability to enter plant tissue where nematodes are embedded.

In a trial against the foliar nematode *Aphielenchoides fragariae* on Hosta plants, at the rate of 3.2 fluid ounces per 10 U.S. gallons water, KT-19827 was significantly more effective than Avermectin, in fact numerically twice as effective using Fischer's LSD multiple Comparison Test. In addition, the KT-19827 treated Hosta leaves were free of fungal foliar diseases and leaf senescence, which were present on the untreated control leaves.

In another trial, no control of the nematode *Aphielenchoides frageria* on Anemone vitfolia was found as to nematode count when measured by repeated measure analysis of variance (ANOVA) and non-parametrid Kruskal-Wallis ANOVA for either KT-19827 or Avermectin. However, the 3.2 ounce rate KT-19827 treated plants showed two-thirds fewer symptomatic leaves than the untreated control and about one-half as many symptomatic leaves as the Avermectin treated plants. The symptomatic leaf analysis was done at the end of the 12 week trial period, during which 6 sprays were applied at 2 week intervals. ANOVA was the analytical measurement methodology.

EXAMPLE a-4

Long Term Control of *Xanthomonas* on *Geraniums*

*Xanthomonas* can be controlled in a commercial greenhouse geranium crop by removing all visibly diseased plants and applying a high dosage rate of 5 fluid ounces per 10 gallons water of KT-19827 done as a spray to run-off using hydraulic spray equipment. Three to five days later any new visibly diseased plants should be removed again and the spray should be repeated. Two or three such sequences are usually sufficient to stop the disease without further recurrence, even after months without further treatment. When treated in this manner, the plants are induced to resist further pathogenic outbreaks of *Xanthomonas* for the remainder of the crop cycle in the greenhouse, a term that far exceeds the pesticide preventive reach of KT-19827. Apparently, KT-19827 treatments induce the plants to resist further pathogenic outbreaks of *Xanthomonas*. This process may be or may not be similar in effect to what are know as Systemic Activated Resistance (SAR) products do. Previously, *Xanthomonas* was considered an uncontrollable disease of geraniums, requiring disposal of the whole crop.

EXAMPLE A-5

KT-19827 Compared with an SAR on Pear with *Erwinia*

Systemic Activator Resistance (SAR) materials affect the treated plant so it resists outbreaks of disease over longer periods of time. KT-19827 was compared with a leading commercial SAR called Bion or Actiguard (Acibenszolar-S-Methyl by Novaritis) against *Erwinia Amylovora* on pear trees, variety "*Butirra*". The test was for the full growing season. Efficacy against *Erwinia* on the trees and fruit was 98% for KT-91827, 73.6% for Bion and zero on the untreated control pear trees. Standard label rates for each product were applied as a foliar spray in an equal manner.

At harvest, 4 out of 250 packets of harvested pears from the KT-19827 plot showed evidence of disease, compared to 17 out of 238 packets showing evidence of disease from the BION plot and to 49 out of 231 packets showing evidence of disease from the untreated trees, which served as controls. The study was not designed to measure the comparative quantity of pears produced on the three plots.

EXAMPLE A-6

Induction of Increased Crop Yield

The novel ability of KT-19827 to induce increase crop yield of treated host plants is demonstrated by a study originally conducted to determine the effectiveness of KT-19827 in *Xanthomonas* on tomatoes.

KT-19827 (PHYTON-27) was applied at 1 fl. oz. per 10 gallons to the 52 row plot. It was compared to a 56 row plot treated with the standard commercial products Kocide and Mancozeb. Chemical applications were made approximately every four days over a two month period. The data for the Kocide-Mancozeb plot is adjusted by 7% to be comparable to the KT19827 plot. Results show that KT-19827 produced an unexpected increase in yield when compared to the commercial products.

|  | Kocide & Mancozeb Actual | K/M adjusted by 7% | Phyton-27 plot actual | Phyton-27 yield increase |
| --- | --- | --- | --- | --- |
| Total bins picked | 178 | (166) | 216 | 23% |
| Picked actual Wt. (lbs.) | 183,820 | (170,953) | 216,665 | 21% |
| Packed actual Wt. (lbs.) | 145,350 | (135,176) | 166,800 | 19% |
| Packed/crop row (lbs.) | 2,596 | — | 3,207 | 21% |
| Cull | 21% | — | 23% | — |

When taking into account the 7% plot size difference, the pick and peck weights indicate about a 20% greater yield in the Phyton-27 crop.

EXAMPLE A-7

Induction of Improved Crop Yield: Pears and Grapes

Field trial of KT-19827 against *Erwinia* (Fireblight) on pears provided very good results plus the unexpected collateral benefit of more fruit. In a replicated study with controls, 10 foliar sprays were applied between March and August at times most useful to control the disease in the course of the season's adverse weather variables which encourage *Erwinia*. By the time of harvest, the normal state of distress of the trees' photosynthetic activity with standard copper bactericides such as copper oxychloride or the classic Bordeau mixture was missing. The consequences of this physiology were very evident at the time of harvest quantitatively and qualitatively.

Subsequently, a field trial of grapes was set up to quantify increased yield on vines treated with KT-19827 sprayed 8 times during the growing season to control mildews and Botrytis, which are major diseases of grapes. One site had plots treated with 7 other standard products, and another site had one standard control. The KT-19827 disease control was better than the standards, plus the yield of grapes by weight were 30% and 22% greater at the two sites respectively. Both sites experienced a 20% increase of sugar levels. The increase in alcohol production corresponded to the combination of both factors—more grapes and more sugar per grape.

EXAMPLE A-8

Prevention of Frost Damage and Rejuvenation of Plants

Spray application of KT-19827 at the rate of about 2 ounces per 10 gallons water on frozen strawberry plants significantly reduces bloom damage, by killing ice-nucleating bacteria, which cause most of the damage associated with frozen plants. In the case of a Japanese Maple tree where freezing temperatures near the ground froze the lower branches, a spray of KT-19827 promptly after the frost desiccated the partially damaged tissue and thereby contained the damage.

EXAMPLE A-9

Use of KT-19827 as Disinfectant

*Erwinia carotovora* subsp. *carotovora*, a destructive pest of many economic crops, can be found residing on ebb and flow greenhouse benches and in fertigation solutions, which recirculate over them. The bacterium also resides in water and in fertigation solutions being transferred to healthy plants in which it subsequently causes disease that KT-19827 is known to control. Efficacy of KT-19827 was compared to three other copper containing materials.

The *Erwinia* inoculum grown on LPGA plates contained 7.0 g of dextrose, 7 g of bacto peptone, 7 g of yeast extract and 15 g of agar per liter and pH adjusted to 6.2 using NaOH. Cultures two days old were used to prepare a bacterial suspension in a sterile 100 mL saline (0.52 g NaCl/L) solution, which was then diluted with saline to 1.2×10 CFU/mL. From the latter solution, 1.0 mL was added to a 9.0 mL saline solution mixed with a copper-based bactericide to obtain a solution containing either 0, 0.5, 1, 2, 4, or 8 ppm of CU++. The chemicals were KT-19827 (copper sulphate pentahydrate, 5.5% metallic Cu), fixed copper (copperoxychloride, 50% metallic Cu) or copper hydroxide, 24.4% metallic Cu and analytical grade copper chloride. The initial dilutions were based on a previously published method for determining the amount of cupric ions present in the different compounds using a Cu 2+-ion specific electrode. For 1 ppm of Cu 2+, one required 3.2 g of Fixed Copper/L; 0.3 ml of Phyton-27/L; or 5.0 g of Champ II/L of solution. For analytical copper chloride, it was assumed that all copper ions were in the cupric form (2.6 mg of CuCl2.2H2O/L+1 ppm of Cu2+). At different timed intervals (5, 10, 20, 30 min., 1, 4, 24 and 48 hrs) after adding the inoculum to the Cu-solutions, 50 ul aliquots were taken from each of the prepared Cu-solutions, and transferred to LPGA plates in triple replicate. The plates were then placed in an incubator maintained at 24 degrees C. After 48 hours of incubation, the colonies were counted, and this number was used to calculate the survival number of bacteria/ml at different times and concentrations. Each bactericide was tested at a different date. The trial was repeated once.

Results show that KT-19827 provided a level of *Erwinia* control that was unexpected. Complete control was attained with KT-19827 after exposure for 30 minutes, at 1.0 ppm of Cu2+, the equivalent of KT-19827 4 oz. per 100 gallons. All other materials tested were less effective at the 1.0 ppm Cu2+rate. Control of *Erwinia* by KT-19827 in the inanimate setting was obtained at a rate far below rates which control disease in plants, which typically are between 20 and 50 oz. per 100 gallons water.

EXAMPLE A-10

(Control of Yeast)

A trial was conducted to determine the effectiveness of KT-19827 for control of the health hazard *Cryptococcus neoformans*, a yeast often growing in pigeon droppings under roosts in old structures. The spores present an aerosol-borne hazard to humans and other animals.

Twenty-two environmental isolates and 6 human isolates of *C. neoformans* were exposed to KT-19827 at 6.4, 3.2, or 1.6 oz. per 10 gallons. All 28 isolates were prepared in tube dilutions to a concentration of $1.0\times10^6$ CFU/mL. The Center for Disease Control, Atlanta, reported this is the first instance of any alternative to Formalin as a control of this disease. Results show that KT-19827 unexpectedly killed all 28 of the human and animal pathogen *C. neoformans*.

| Concentration of KT-19827 (oz. per 10 gal. water) | Number of *C. neoformans* isolates killed. 28 were tested |
|---|---|
| 1.6 | 4 |
| 3.2 | 28 |
| 6.4 | 28 |

It is apparent that many modifications and variations of this invention as hereinbefore set forth may be made without departing from the spirit and scope thereof. The specific embodiments described are given by way of example only and the invention is limited only by the terms of the appended claims.

The invention claimed is:

1. A method of disinfecting greenhouse ebb and flow bench surfaces, which method comprises introducing to the greenhouse ebb and flow bench surface a small but effective amount of a tannate complex selected from the group consisting of the tannate complex of picro ammonium formate and the tannate complex of picro cupric ammonium formate in aqueous solution combined with a minor amount of a surfactant sufficient to prevent formation of ammonium picrate.

2. A method according to claim 1 wherein said tannate complex is applied at the rate of about 12 to 55 ounces per 100 gallons of water.

3. A method according to claim 1 wherein said tannate complex is the tannate complex of picro cupric ammonium formate applied at the rate of about 15 to 30 ounces per 100 gallons of water.

4. A method according to claim 1 wherein said tannate complex is introduced to the greenhouse ebb flow bench surfaces by spraying, wiping, drenching, or soaking.

5. A method according to claim 1 wherein greenhouse ebb and flow bench surfaces are disinfected by applying said tannate complex to the surfaces.

* * * * *